(12) United States Patent
Kim

(10) Patent No.: US 6,471,714 B1
(45) Date of Patent: Oct. 29, 2002

(54) APPARATUS AND METHOD FOR MANUARY ACCESS TO SUFFLATED BODY CAVITY

(76) Inventor: H. Charles Kim, 32 Merry Hill Ct., Baltimore, MD (US) 21208

( * ) Notice: Subject to any disclaimer, the term of this patent is extended or adjusted under 35 U.S.C. 154(b) by 0 days.

(21) Appl. No.: 09/546,611

(22) Filed: Apr. 10, 2000

(51) Int. Cl.[7] .............................. A61B 17/08; A61D 1/00
(52) U.S. Cl. ........................ 606/213; 606/215; 606/192; 606/191; 604/237; 604/167; 128/897; 128/850
(58) Field of Search .............................. 606/213, 215, 606/192, 191; 604/237, 167; 128/897, 850

(56) References Cited

U.S. PATENT DOCUMENTS 5,813,409 A * 9/1998 Leahy et al. ................ 128/850
6,033,428 A * 3/2000 Sardella ...................... 606/213

\* cited by examiner

Primary Examiner—Danny Worrell
Assistant Examiner—Robert Muromoto, Jr.

(74) Attorney, Agent, or Firm—Rosenberg, Klein & Lee (57) ABSTRACT

There is provided an apparatus (10) and method for maintaining manuary access to a sufflated body cavity of a patient through a fenestration formed in the patient's body tissue during a minimally invasive surgical procedure. The apparatus (10) generally comprises a seal section (100) and a sheath section (200) coupled thereto. The seal section (100) includes an endless loop portion (110) that defines an opening (120). The sheath section (200) includes a mouth portion (210), a glove portion (230), and a pliable intermediate portion (220) extending therebetween. The intermediate portion (220) maintains in reconfigurable manner a substantially gas impermeable barrier between the mouth and glove portions (210, 230) when the glove portion (230) is passed through the opening (120) into the body cavity responsive to manuary actuation. The passage of the glove portion (230) through the opening (120) biases at least a part of the intermediate portion (220) to engage the patient's body tissue immediately bounding the fenestration, whereby the sufflation of the body cavity is substantially preserved during the minimally invasive surgical procedure.

22 Claims, 4 Drawing Sheets

APPARATUS AND METHOD FOR MANUARY ACCESS TO SUFFLATED BODY CAVITY

BACKGROUND OF THE INVENTION

1. Field of the Invention

The present invention is generally directed to an apparatus and method for facilitating a minimally invasive surgical procedure. More specifically, the subject apparatus and method is directed to facilitating manuary access to a sufflated body cavity during a hand-assisted laparascopic or other surgical procedure.

Minimally invasive surgical procedures such as laparascopic surgery have gained wide acceptance in various medical fields over traditional, filly invasive procedures for somewhat readily apparent reasons. Not only does the minimal invasiveness of such procedures significantly reduce the pain and stress to which a patient is otherwise subjected, they measurably reduce both the severity and duration of the recuperative period following surgery. The resulting benefits both in terms of cosmetic results and cost savings—are often quite considerable. Moreover, because they permit the required surgical manipulations to be carried out with the naturally enclosed biophysical environment at the surgery site kept substantially intact, such procedures minimize considerably the patient's exposure to potentially infectious or toxic organisms and contaminants. This, in turn, substantially minimizes the patient's risk of suffering medical complications.

In a typical laparoscopic surgical procedure, access to the surgery site—the abdominal or other internal body cavity, for instance—is gained through one or more fenestrations formed by puncturing the skin and the underlying muscle and soft tissue layers. A suitable miniature scope is introduced into the body cavity along with one or more laparoscopic instruments through shared or separate fenestrations. The surgeon may then perform the required surgical procedure by manipulating the laparoscopic instrument(s) and/or scope while acquiring visual feedback by viewing a video image of the site, as captured by the scope and reproduced on a display monitor.

As widely accepted and prevalent as they have become, however, such surgical procedures are not without their limitations. The surgeon's ability to adequately effect the precise cutting, suturing, and other very delicate surgical manipulations invariably required during laparoscopic procedures, for example, is highly dependent upon a set of critical factors including: the extensive experience and acute dexterity of the surgeon in performing the coordinated manipulations of the numerous laparoscopic instruments at hand; the degree of visibility attainable with the scope; and, the practical range of utility of the given instruments. A deficiency in any one of these factors severely obstructs the given procedure's successful completion and may, under certain circumstances, give rise to life threatening conditions. Hence, it not too infrequently becomes necessary to unexpectedly convert during the course of surgery to a fully invasive, open surgery.

Also, adhesions between the patient's internal organs at or around the surgery site tend to block or otherwise hinder the free manipulability of the laparoscopic instruments. It is difficult in such cases to maneuver an instrument between the adhering organs without potentially causing harm to either the organs or the instrument. Even where it is possible to adequately circumvent the adhering organs, much time and effort are unduly expended.

Of the more general limitations is the unavailability to the surgeon of any direct tactile sense of the surgery site. The instantaneous assessments that the surgeon must continually make as the surgical procedure progresses is consequently hindered by the lack of a key component of sensual feedback. The practicability of laparoscopic and like procedures is thus unduly restricted.

An approach developed to address these limitations is the so-called hand-assisted procedure, wherein the surgeon actually inserts a free hand into the given body cavity through a fenestration. With this free hand, the surgeon is able to supplement indirect, instrument-effected manipulations of organ and tissue parts with direct, hand-effected manipulations. Such direct hand manipulations often aid enormously in effecting difficult manipulations of organ and tissue that may otherwise be problematic using laparoscopic instrument maneuvers alone. With the free hand, the surgeon is also able to supplement the visual feedback acquired via the laparascopic scope with tactile sense feedback. Such supplemental feedback yields a vital source of additional information for either confirming or correcting visual assessments which, alone, may leave lingering ambiguity and general uncertainty.

While this manuary access to the surgery site greatly facilitates the conduct of minimally invasive surgical procedures, it too presents significant potential drawbacks and difficulties. First and most obvious, it necessarily compromises to some unavoidable extent the minimal invasiveness of the procedures. More notable than that, however, the sizable fenestration necessary to accommodate the manuary access threatens to compromise the body cavity's vital sufflation.

Consequently, there is a need for a method and apparatus by which a surgeon may safely and securely gain manuary access to an internal body cavity during a hand-assisted minimally invasive surgical procedure. There is a need for such method and apparatus that sufficiently establishes and maintains a substantially airtight seal across the fenestration which admits the surgeon's hand into the body cavity, yet does not unduly restrict or restrain the hand's movements. There is, furthermore, a need for such method and apparatus which is simple, convenient, and economical to utilize.

2. Prior Art

Devices are known in the art for facilitating manuary access to an internal body cavity during hand-assisted laparoscopic surgical procedures. For instance, in U.S. Pat. No. 5,853,395 issued to Crook et al., an assembly is disclosed for providing extracorporeal pneumoperitoneum. The assembly includes a multi-part support ring structure which is adhesively affixed to the patient's abdominal surface surrounding the given fenestration; a collar-like wound protector which is inserted to line the exposed edges of the fenestration; and a flexible sleeve member about an open end of which a seal ring is attached. During use, the seal ring of the sleeve member is secured in sealed manner to the ring structure. The surgeon's hand, wearing a surgical glove, is passed to engage finger holes formed into an otherwise closed end of the sleeve member, then advanced first through the engaged seal ring and its supporting ring structure, and next through the wound protector, into the internal body cavity. The gas escaping through the fenestration is captured by the sleeve member, which is sealed and retained in place cooperatively by the seal ring and supporting ring structure.

While this assembly does enable manuary access to the internal body cavity, and even seeks to preserve pneumoperitoneum during that access, it nonetheless suffers from a number of very notable drawbacks which, in practice, diminish its utility. First, the assembly is quite substantial both in the number and complexity of its components. This not only further complicates matters for the surgeon already burdened by the numerous concerns relating to the surgical procedure at hand, it makes for a cumbersome structure that consumes an inordinate share of the precious area on the surface of the patient's abdomen—area necessary to adequately accommodate fenestrations for the passage of other instruments into the internal body cavity. Second, proper operation of the assembly hinges upon the support ring structure remaining adhesively affixed to the patient's abdominal skin surface throughout the surgical procedure which typically lasts hours on end. During the course of surgery, however, the cumulative effects of moisture, movements of the surgeon's hand, and other factors often erode the structure's adhesiveness to the point that it actually detaches from the patient's skin surface, thereby compromising the seal and openly exposing the surgery site to contaminants. What is more, adequate remedial measures are not readily available at that point, for it is extremely difficult to re-adhere the structure to the skin surface once adhesion is initially lost.

An additional drawback of note is the presence of openings in the form of finger holes formed at one end of the sleeve member. The holes require that the surgeon's hand be additionally covered by a separate surgical glove. Given that they would otherwise permit leakage, the holes also require that the surgeon's hand be covered by both a first, or inner, surgical glove prior to passage of the fingers and thumb therethrough, and a second, or outer, surgical glove following passage of the fingers and thumb therethrough. The tightly fitting extraneous layers thus required about the surgeon's hand, in addition to being highly inconvenient to adorn, serve very undesirably to constrict the surgeon's hand and constrain its movements—consequently heightening the discomfort experienced by the surgeon as well as the effort exerted by him or her. The extraneous layers also dull the covered hand's sensitivity, severely limiting the degree of useful sensual feedback that the surgeon might otherwise acquire by touch.

Another device known in the art is one disclosed in U.S. Pat. No. 5,480,410 issued to Cuschieri et al. for an extracorporeal pneumoperitoneum access bubble. The device forms a balloon-like spherical dome structure having a bottom opening whose neck is passed through a fenestration to serve as a conduit for insufflation gas migrating from the abdominal cavity. Thus maintained in an inflated state, the dome portion has formed therein a plurality of valves which permit access to various instruments without permitting significant leakage of the insufflation gas.

The device permits access also to a surgeon's hand, provided that the admitting valve formed in the dome portion is of sufficiently great size. The device, nonetheless, suffers from a number of the practical drawback s suffered by other similar devices known in the art. First and most obvious, the valve openings which permit access to instruments as well as the surgeon's hand necessarily interrupt the gas impermeable barrier extending over and about the fenestration. While they are designed to minimize it, the valve openings invariably permit leakage when accommodating an implement passed therethrough, especially since they are subjected to disturbing forces by the implements' manipulation during a given surgical procedure. This leakage would occur all the more where a valve opening is of extraordinary size—as it must be to accommodate the surgeon's hand and forearm; and where a valve opening is subjected to a substantial degree of disturbance—as would be caused by the surgeon's hand and forearm movements.

Another drawback is found in the considerable space necessarily occupied by the device's dome portion. The expansive volume permits few, if any, other instruments to share surrounding areas of the patient's abdominal skin surface. Indeed, the plurality of valve openings formed in the dome portion seemingly encourages common use of the device to admit multiple instruments into the abdominal cavity. Where additional instruments must be introduced into the abdominal cavity through neighboring fenestrations, in any event, the task becomes rather awkward, with the prevailing likelihood—even if neighboring instruments may be adequately introduced—of inadvertently making interfering contact with them.

Yet another drawback resides in the lack of adequate measures for maintaining the device sufficiently in place. As the insufflation gas migrates into and collects within its dome portion, the device is internally subjected to the intra-abdominal pressure that maintains insufflation of the abdominal cavity. With its resulting balloon-like structure, then, the device becomes somewhat unstable in its disposition, and tends in practice towards expulsion from its engagement with the fenestration.

SUMMARY OF THE INVENTION

It is a primary object of the present invention to provide an apparatus and method whereby a surgeon may safely and securely gain manuary access to an internal body cavity during a hand-assisted minimally invasive surgical procedure.

It is another object of the present invention to provide an apparatus and method whereby a substantially air-tight seal is substantially maintained across a fenestration that admits a surgeon's hand into an internal body cavity during a hand-assisted minimally invasive surgical procedure.

It is yet another object of the present invention to provide an apparatus and method whereby manuary access to an internal body cavity may be gained without undue restriction or restraint of the surgeon's hand movements.

It is still another object of the present invention to provide an apparatus and method which is both simple and convenient to utilize.

These and other objects are attained in the apparatus and method of the present invention for maintaining manuary access to a sufflated body cavity through a fenestration formed through a patient's body tissue during a minimally invasive surgical procedure. The apparatus of the present invention generally comprises a seal section and a sheath section formed of a substantially gas impermeable material coupled thereto. The seal section includes an endless loop portion defining a first opening. The loop portion is formed with an engagement surface for engaging in substantially flush manner an inner wall surface of the sufflated body cavity adjacent the fenestration. The sheath section includes a mouth portion, a glove portion, and a pliable intermediate portion collapsibly extending therebetween. The mouth portion is coupled to the loop portion of the seal section and defines a second opening aligned in open communication with the first opening. The intermediate portion maintains in reconfigurable manner a substantially gas impermeable barrier between the mouth and glove portions when the glove portion is passed through the first and second openings into the body cavity responsive to manuary actuation. This passage of the glove portion through the mouth and loop portions sufficiently deflects sufflation gas to bias at least a part of the intermediate portion into substantially conforming engagement of the patient's body tissue peripherally bounding the fenestration. The sufflation of the body cavity is thus substantially preserved during the minimally invasive procedure.

In a preferred embodiment, the glove and intermediate portions of the sheath section are integrally joined. The seal section in that embodiment is contoured substantially as an annular ring, and is formed of a resilient material.

DESCRIPTION OF THE PREFERRED EMBODIMENTS

Figure 1:
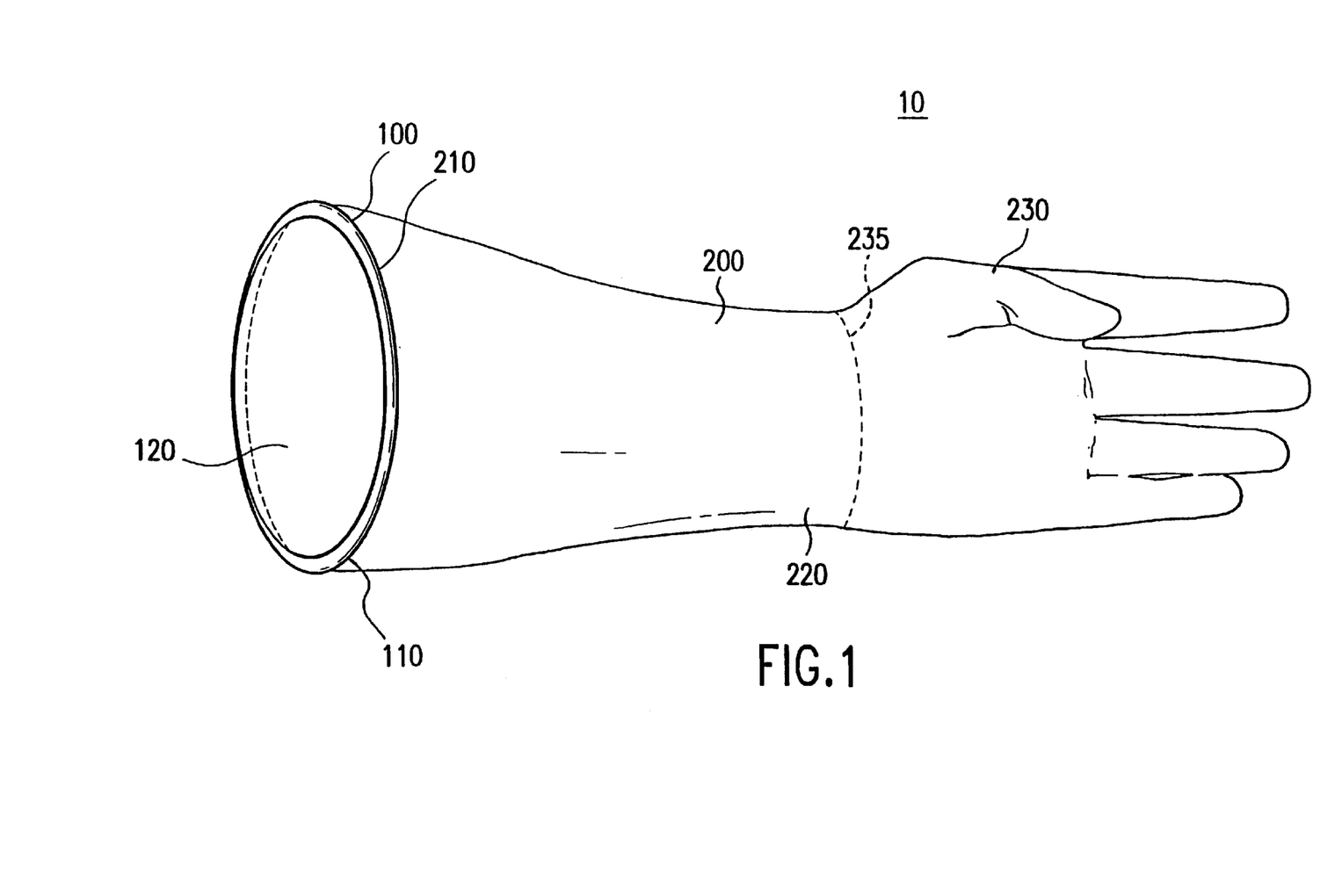
FIG. 1 is a perspective view of one embodiment of the present invention.

Referring now to FIG. 1, there is shown one embodiment of the subject manuary access apparatus 10. Manuary access apparatus 10 generally includes a seal section 100 coupled to a sheath section 200. Seal section 100 is preferably formed with an endless loop configuration realized with any suitable shape known to sufficiently effect sealed engagement with a soft bodily tissue surface. In the embodiment shown, seal section 100 is preferably formed with a ring-shaped contour which defines an annular engagement surface whose arcuate sectional contour may effectively maintain sealed engagement with the smooth, yet non-flat, tissue lining surfaces typically encountered within a human anatomy. Seal section 100 is preferably formed with a resilient bias towards an annular or other encircling configuration about an opening 120, such that it readily springs to its original configuration once it is fully introduced into a patient's internal body cavity after undergoing deflection and deformation during passage through an incision-formed fenestration.

Seal section 100 is fabricated by any suitable means known in the art of a resilient material that is substantially impermeable to both liquid and gas. It is preferably formed of a material containing rubber, plastic, or any other suitable composition which exhibits sufficient resilience and liquid/gas impermeability. The material is preferably one which is capable of withstanding continuous extended exposure to the biochemical environment that it would typically be subjected to during use in the intended application, and which tends not to cause irritation or other significant ill effects in the bodily portions it contacts during that use.

Seal section 100 is preferably fabricated separately and joined to sheath section 200 via a thermally welded joint or via any other suitable measures known in the art. Seal section 100 may, alternatively, be integrally formed with sheath section 200. It is important, in any event, that sufficient measures be taken to avert the compromise in either the strength or seal realized at the joint (or transition region) between the sections 100, 200.

Sheath section 200 is generally formed as a protective covering for the surgeon's hand and forearm to be introduced into the given body cavity. As such, it is formed generally of a flexible, pliable material substantially impermeable to liquid and gas which closely conforms to at least the hand inserted therein, but does not substantially constrict nor restrict the movements of either the hand or forearm.

Sheath section 200 includes a mouth portion 210 coupled to loop portion 110 of seal section 100; a glove portion 230; and, a pliable intermediate portion 220 collapsibly extending therebetween. Mouth portion 210 is preferably formed to follow the endlessly looped contour of loop portion 110, such that it defines an opening which coincides with opening 120. Mouth portion 210 is intimately coupled to loop portion 110 in sealed manner by either integral formation therewith or by any suitable adjoining measure. The coupling itself is of sufficient strength and durability to resist compromise when subjected to various stresses during use upon manipulations of the intermediate and glove portions 220, 230.

Extending from and preferably formed integrally with mouth portion 210 is a pliable intermediate section 220. As it serves in accordance with the present invention to reconfigurably maintain, during use, a barrier substantially impermeable to gas across the space immediately surrounding the surgeon's hand and forearm, it is important that intermediate section 220 be readily collapsible and extendable. Those properties enable intermediate section 220 to adaptively reconfigure responsive to hand and forearm movements while preserving the seal established across the hand-admitting fenestration.

Preferably, intermediate section 220 is formed of a thin material containing a plastic, rubber, or other liquid/gas impermeable material of suitable strength, durability, and pliability. It is preferably of sufficiently low material weight that it may be freely drawn partially inside out to accommodate the mouth portion's insert into the body cavity (with seal section 100) prior to the glove portion's insert. It is preferably of such sufficiently low material weight, also, to freely yet captively extend responsive to the pressure of the sufflation gas from the internal body cavity which would otherwise escape through the fenestration when the surgeon's hand is admitted therethrough. As the surgeon's hand and forearm are moved within the fenestration and body cavity during the course of surgery, then, intermediate section 220 reconfigurably captures a surrounding pocket of sufflation gas.

Preferably, though certainly not essentially, intermediate section 220 is formed of a translucent material. In addition to permitting the entry of illuminating light into the body cavity, this enhances the visibility into the cavity available to the surgeon.

Glove portion 230 is formed of a material having the liquid/gas impermeability, strength, and durability of the other portions 210, 220. It is preferably formed, however, of a sufficiently elastomeric material to snugly conform to the thumb and fingers of the surgeon's hand, in order that their sensitivity and mobility may remain substantially unhindered. It may be formed in any suitable manner known in the art—in much the same manner, for instance, that typical latex surgical gloves are formed. In accordance with the present invention, however, it is important that glove portion 230 be coupled at its cuff region to intermediate portion 220. It may be integrally formed with intermediate portion 220, or else, intimately joined thereto at joint 235 by any suitable means known in the art, such as by thermal welding or other techniques.

Figure 2:
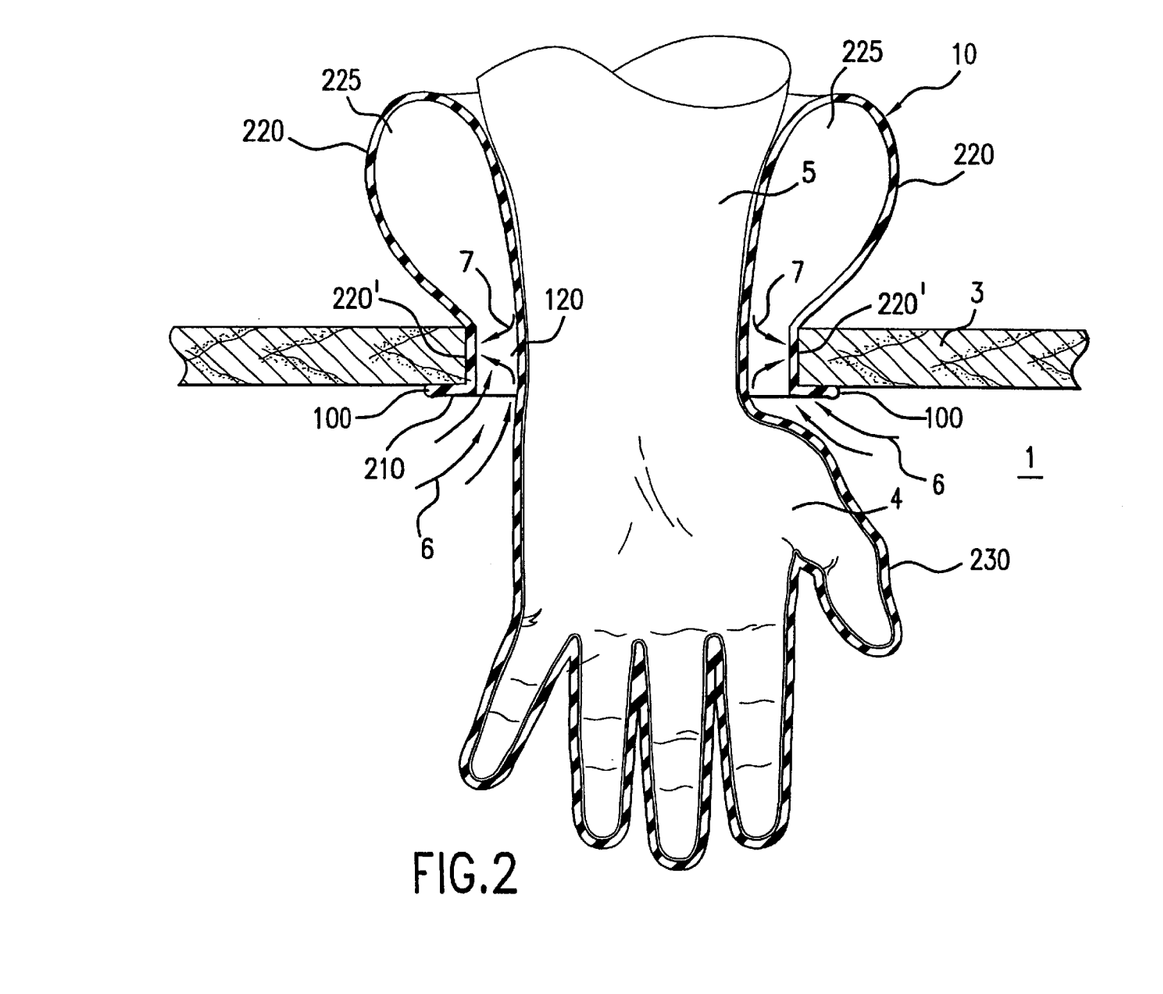
FIG. 2 is a sectional view of the embodiment of the present invention shown in FIG. 1 illustrating an exemplary configuration during use.

In an exemplary abdominal cavity application of apparatus 10 illustrated in FIG. 2, manuary access into a patient's abdominal cavity 1 is gained through a fenestration 2 formed by incision through the patient's skin and underlying layers of tissue—collectively referred to herein as the "abdominal wall" 3 in the application illustrated. Seal section 100 is passed through the fenestration 2 and positioned beneath the abdominal wall 3 to bear against, and form a substantially sealed engagement with, the abdominal wall's inner lining layer 3'—the peritoneum in the case of the abdominal cavity. To accommodate this, sheath section 200 is at least partially drawn to an inside-out configuration. Once the surgeon's hand 4 and forearm 5 are inserted into sheath section 200 and thereafter admitted into the abdominal cavity 1 through the opening 120 of seal section 100 as shown, intermediate portion 220 then forms a gas-capturing pocket 225 about the surgeon's forearm 5. Sufflation gas (normally maintained at a regulated pressure within the abdominal cavity 1 during surgical procedures) that might otherwise escape through open portions of the fenestration about the hand 4 and forearm 5, is then retained by the pocket 225. Subsequent movements of the surgeon's hand 4 or forearm 5 cause the redistribution of the sufflation gas trapped within the pocket 225, but do not cause its escape.

The retention of sufflation gas by intermediate portion 220 at the pocket 225 provides another advantage in accordance with the present invention. The upward force applied to seal section 100 by the sufflation gas pressure, or intra-abdominal pressure, maintained within the abdominal cavity 1 which urges it against the inner lining of the abdominal wall 3 is further augmented by the entrapment of sufflation gas at the pocket 225. The sufflation gas pressure at that pocket 225 causes intermediate portion 220 to draw seal section 100 upward, thereby reinforcing its sealed engagement of the abdominal wall 3 inner lining.

If left unchecked, however, the collective upward force upon apparatus 10 could very well lead to its expulsion from the fenestration altogether. Thus, in accordance with the present invention, the passage of sheath section 200 through the opening 120 of seal section 100 (into the abdominal cavity 1) forced by the surgeon's hand 4 and forearm 5 deflects sufflation gas migrating between the abdominal cavity 1 and the pocket 225 against that part 220' of intermediate portion 220 lining the soft body tissue peripherally bounding the fenestration, as indicated by the directional arrows 7. This yields an outwardly directed pressure which biases the part 220' into substantially conforming engagement of the fenestration-bounding body tissue. Both the device's seal preserving capability and its retention within the fenestration are thereby augmented. Thus, apparatus 10 serves to securely preserve an uninterrupted seal across the fenestration 2, while affording substantially free mobility to both the surgeon's hand 4 and forearm 5 within the confines of the fenestration 2 and abdominal cavity 1.

The simplicity of apparatus 10, both in structure and function, affords other significant advantages which may not be readily apparent. For instance, its spacial requirements during use do not extend significantly beyond a fenestration broad enough to admit the surgeon's hand and forearm. This yields as much surrounding area of the abdominal or other given surface on the patient's body to accommodate the separate fenestrations necessary for the passage of other instruments into the given internal body cavity. Hence, the 'overcrowding' of the surgery area typically encountered in hand-assisted minimally invasive procedures is considerably minimized—along with the attendant safety risks of inadvertent interference of neighboring instruments, restricted ranges of mobility, and the like.

Figure 3:
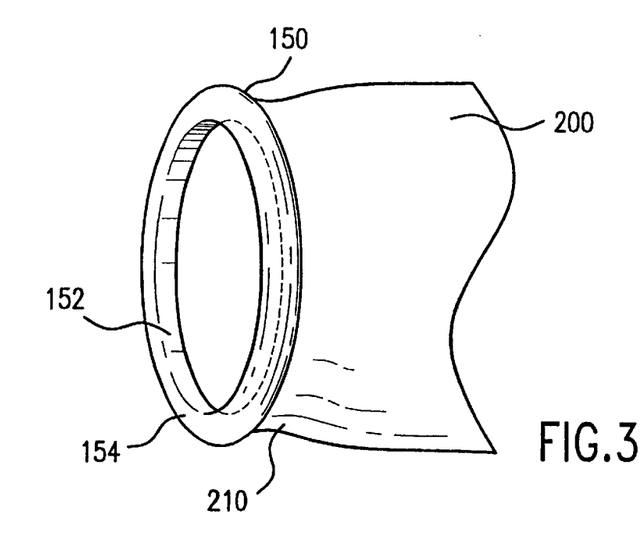
FIG. 3 is a perspective view, partially cut away, of a portion of a second embodiment of the present invention.
Figure 4:
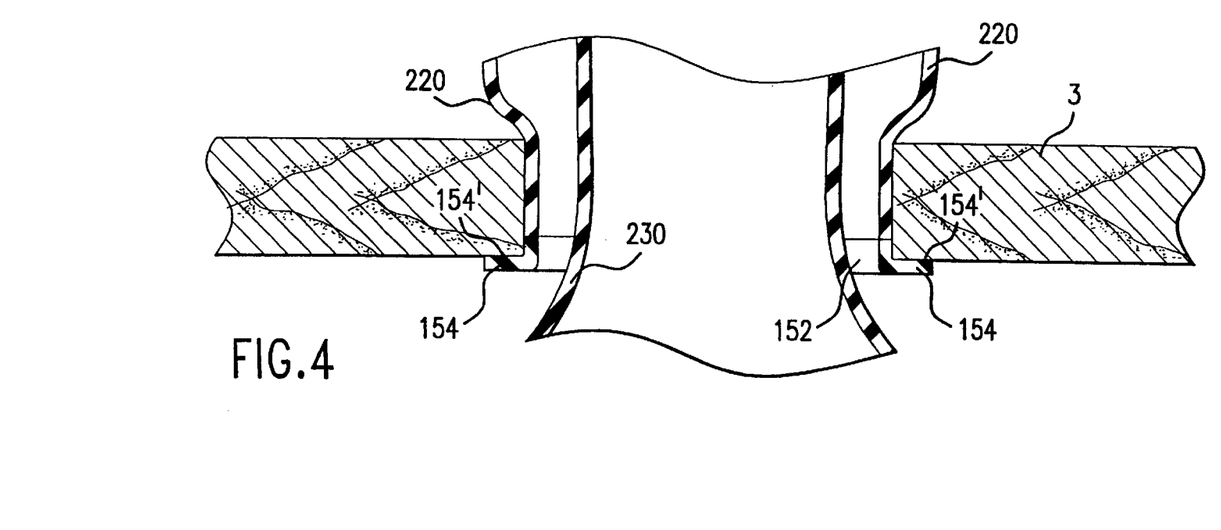
FIG. 4 is a sectional view of the second embodiment of the present invention shown in FIG. 3 illustrating an exemplary configuration during use; and, FIG. 5 is a sectional view of a third embodiment of the present invention illustrating an exemplary configuration during use.

Referring now to FIGS. 3–4, there is shown a seal section 150 formed in accordance with an alternate embodiment of the present invention. While preferably similar in material composition and properties as seal section 100 described with reference to the embodiment shown in FIGS. 1 and 2, seal section 150 in this embodiment includes an annular collar portion 152 coupled as before to mouth portion 210 of sheath section 200. Seal section 150 further includes an outwardly flared flange portion 154 extending from collar portion 152, whose upper surface 154' engages the inner lining of the abdominal wall 3 in substantially flush manner.

Figure 5:
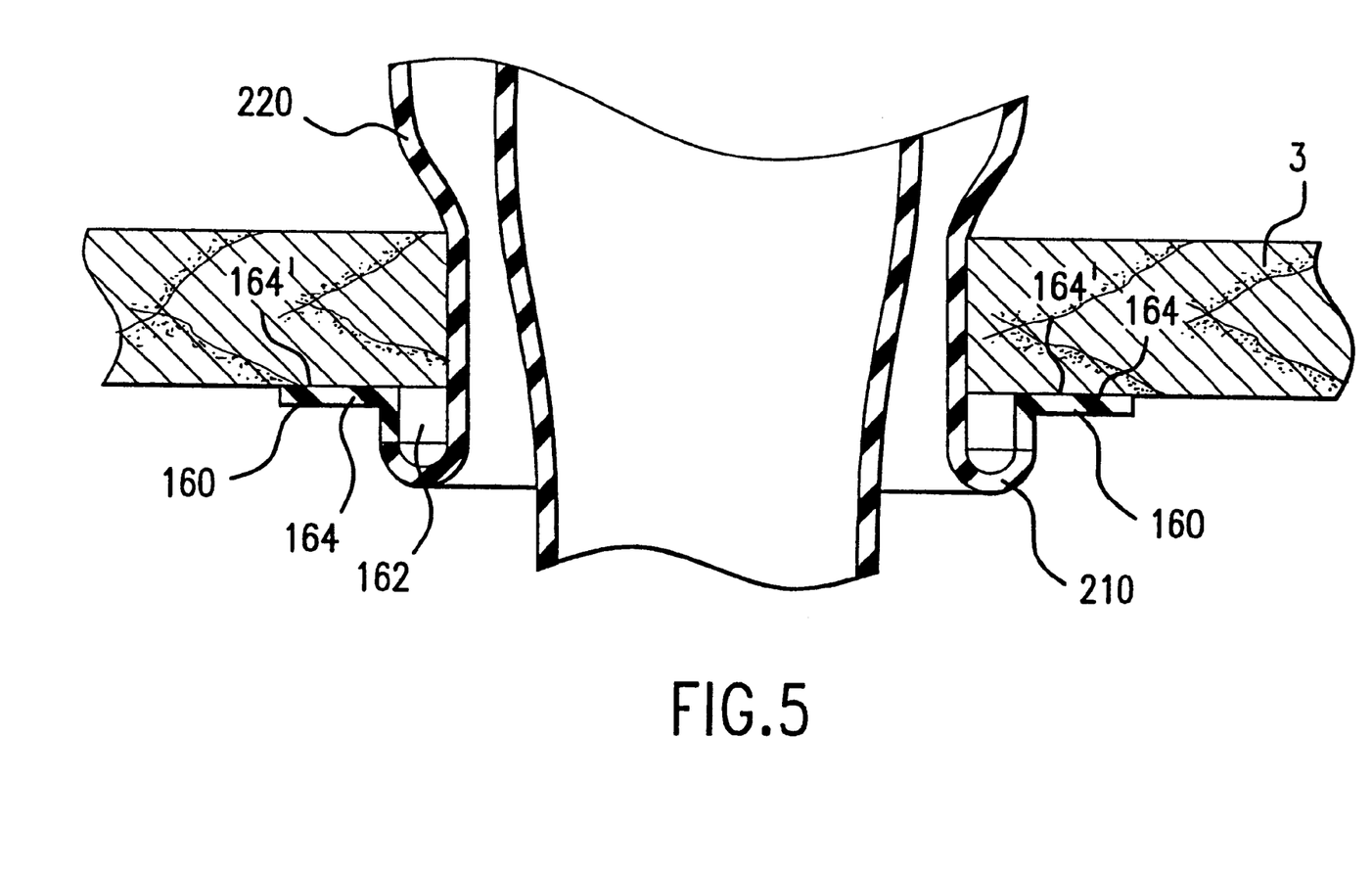

Numerous other configurations may be employed for the seal section. In another alternate embodiment shown in FIG. 5, for example, seal section 160 is similar in configuration to seal section 150 shown in the embodiment of FIGS. 3–4, but orientated in inverted manner relative to intermediate section 200 and dimensioned accordingly. Seal section 160 includes an annular collar portion 162 coupled to mouth portion 210 of sheath section 200. Seal section 160 further includes an outwardly flared flange portion 164 extending from collar portion 162, whose upper surface 164' engages the inner lining of the abdominal wall 3 in substantially flush manner.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described; certain features may be used independently of other features; and, in certain cases, particular combinations of method steps may be reversed or interposed, all without departing from the spirit or scope of the invention as defined in the appended Claims.

What is claimed is:

1. An apparatus for maintaining manuary access to a sufflated body cavity through a fenestration during a minimally invasive surgical procedure comprising:
    (a) a seal section including an endless loop portion defining a first opening, said loop portion having formed thereon an engagement surface for engaging in substantially flush manner an inner wall surface of the sufflated body cavity adjacent the fenestration; and,
    (b) a sheath section formed of a substantially gas impermeable material, said sheath section including:
        (1) a mouth portion coupled to said loop portion of said seal section, said mouth portion defining a second opening aligned in open communication with said first opening;
        (2) a glove portion for receiving therein a hand of a user; and,
        (3) a pliable intermediate portion extending between said mouth and glove portions to maintain therebetween a substantially gas impermeable barrier for defining a gas capturing pocket when said glove portion is passed through said first and second openings into the body cavity responsive to manuary actuation, said gas capturing pocket receiving sufflation gas migrating from the body cavity to distend adaptively about said glove portion;
    whereby the sufflation of the body cavity is substantially preserved during the minimally invasive procedure.

2. The apparatus as recited in claim 1 wherein said glove and intermediate portions of said sheath section are integrally joined.

3. The apparatus as recited in claim 2 wherein said sheath section is integrally formed of a composition including a plastic material.

4. The apparatus as recited in claim 3 wherein said sheath section is formed of a substantially translucent material.

5. The apparatus as recited in claim 2 wherein said sheath section is integrally formed of a composition including a rubber material.

6. The apparatus as recited in claim 5 wherein said seal section is formed of a resilient material.

7. The apparatus as recited in claim 6 wherein said engagement surface of said seal section loop portion includes an outwardly extended flange.

8. The apparatus as recited in claim 7 wherein said loop portion of said seal section is substantially annular in contour.

9. The apparatus as recited in claim 6 wherein said loop portion of said seal section is contoured substantially as an annular ring.

10. A hand covering apparatus for maintaining manuary access to a sufflated body cavity of a patient through a fenestration formed in the patient's body tissue during a minimally invasive surgical procedure comprising:
  (a) a resilient seal section including an endless loop portion, said loop portion defining a first opening and having formed thereon an engagement surface for engaging in substantially flush manner an inner wall surface of the sufflated body cavity about the fenestration; and,
  (b) a sheath section formed of a substantially gas impermeable material, said sheath section including:
    (1) a mouth portion coupled to said loop portion of said seal section, said mouth portion defining a second opening aligned in open communication with said first opening;
    (2) a glove portion for receiving therein a hand of a user; and,
    (3) a pliable intermediate portion integrally joined to said glove portion, said intermediate portion extending between said mouth and glove portions for defining a gas capturing pocket when said glove portion is passed through said first and second openings into the body cavity, said gas capturing pocket during the minimally invasive procedure receiving sufflation gas migrating from the body cavity to distend adaptively about said glove portion, said gas capturing pocket remaining at least partially withdrawn from the fenestration and engaging in substantially conforming manner the soft body tissue bounding the fenestration;
  whereby said intermediate portion adaptively maintains a substantially gas impermeable barrier across portions of the fenestration about the user's hand to substantially preserve the sufflation of the body cavity.

11. The apparatus as recited in claim 10 wherein said sheath section is integrally formed.

12. The apparatus as recited in claim 11 wherein said loop portion is configured substantially as an annular ring.

13. The apparatus as recited in claim 12 wherein said sheath section is formed of a composition including a plastic material.

14. The apparatus as recited in claim 12 wherein said sheath section is formed of a composition including a rubber material.

15. The apparatus as recited in claim 11 wherein said loop portion of said seal section includes an annular flange, said annular flange defining said engagement surface.

16. The apparatus as recited in claim 15 wherein said sheath section is formed of a composition including a plastic material.

17. The apparatus as recited in claim 15 wherein said sheath section is formed of a composition including a rubber material.

18. A method of providing manuary access to a sufflated body cavity of a patient through a fenestration formed in the patient's body tissue during a minimally invasive surgical procedure comprising the steps of:
  (a) establishing a seal section including an endless loop portion defining a first opening;
  (b) establishing a sheath section formed of a substantially gas impermeable material, said sheath section having an inner side and an outer side, said sheath section including:
    (1) a mouth portion coupled to said loop portion of said seal section, said mouth portion defining a second opening aligned in open communication with said first opening;
    (2) a glove portion for receiving therein a hand of a user; and,
    (3) a pliable intermediate portion extending between said mouth and glove portions for defining a gas capturing pocket when said glove portion is passed through said first and second openings into the body cavity;
  (c) passing said seal section through the fenestration into the body cavity;
  (d) positioning said loop portion of said seal section in the body cavity to engage in substantially flush manner an inner wall surface of the body cavity adjacent the fenestration; and,
  (e) passing said glove portion of said sheath section through said first and second openings responsive to manuary actuation by a user, thereby deflecting at least a portion of a sufflation gas migrating from the body cavity to bias at least a part of said sheath section intermediate portion against the body tissue immediately bounding the fenestration, said gas capturing pocket defined by said sheath section intermediate portion receiving the sufflation gas to distend adaptively about said glove portion;
  whereby a substantially gas impermeable barrier is reconfigurably maintained between said seal section and said glove portion of said sheath section to substantially preserve the sufflation of the body cavity during the minimally invasive procedure.

19. The method as recited in claim 18 further comprising the step of maintaining said intermediate portion of said sheath section at least partially withdrawn from the fenestration to define a gas-retaining pocket communicating with the body cavity.

20. The method as recited in claim 19 further comprising before step (c) the step of withdrawing said glove portion of said sheath section toward said inner side thereof and away from said first and second openings.

21. An apparatus for maintaining sealed manuary access to a sufflated body cavity through a fenestration during a minimally invasive surgical procedure comprising:
  (a) a seal section including an endless loop portion for retentive placement within the sufflated body cavity, said loop portion defining a first opening and having formed thereon an engagement surface for engaging in substantially sealed manner an inner wall surface of the sufflated body cavity about the fenestration responsive to sufflation gas pressure within the body cavity; and,
  (b) a pliable sheath section formed of a substantially gas impermeable material, said sheath section including:

(1) a mouth portion coupled to said loop portion of said seal section, said mouth portion defining a second opening aligned in open communication with said first opening;
(2) a glove portion for receiving therein a hand of a user; and,
(3) an intermediate portion extending between said mouth and glove portions, said intermediate portion forming an adaptively reconfigurable gas impermeable barrier when said glove portion is passed through said first and second openings into the body cavity, said gas impermeable barrier distensively containing sufflation gas migrating about said glove portion from the body cavity, said distended gas impermeable barrier reinforcing the substantially sealed engagement of said seal section against the body cavity inner wall surface;

said seal and sheath sections being formed in a one-piece configuration;

whereby the sufflation of the body cavity is substantially preserved during the minimally invasive procedure.

22. The apparatus as recited in claim 21 wherein said gas impermeable barrier is distensible annularly about said glove portion during manuary access to the sufflated body cavity.

* * * * *